(12) United States Patent
Ensign et al.

(10) Patent No.: US 9,242,290 B2
(45) Date of Patent: Jan. 26, 2016

(54) METHOD AND APPARATUS FOR CREATING FORMED ELEMENTS USED TO MAKE WOUND STENTS

(75) Inventors: Lance Ensign, Santa Rosa, CA (US); Erik Griswold, Penngrove, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 877 days.

(21) Appl. No.: 13/438,732

(22) Filed: Apr. 3, 2012

(65) Prior Publication Data
US 2013/0255347 A1 Oct. 3, 2013

(51) Int. Cl.
| | |
|---|---|
| A61F 2/86 | (2013.01) |
| A61F 2/88 | (2006.01) |
| B21F 1/04 | (2006.01) |
| A61F 2/90 | (2013.01) |
| B21F 45/00 | (2006.01) |

(52) U.S. Cl.
CPC ... *B21F 1/04* (2013.01); *A61F 2/90* (2013.01); *B21F 45/008* (2013.01); *A61F 2/86* (2013.01); *A61F 2/88* (2013.01); *A61F 2240/001* (2013.01)

(58) Field of Classification Search
CPC ......... B21F 1/04; B21F 45/008; B21D 13/00; B21D 13/02; B21D 13/08; B21D 13/10
USPC ........ 72/379.6, 385, 379.1, 380, 386; 140/90, 140/105
See application file for complete search history.

(56) References Cited

U.S. PATENT DOCUMENTS

| | | | |
|---|---|---|---|
| 2,153,936 A * | 4/1939 | Owens | 140/82 |
| 3,185,185 A | 5/1965 | Pfund | |
| 4,047,544 A | 9/1977 | Seaborn et al. | |
| 4,886,062 A | 12/1989 | Wiktor | |
| 5,019,090 A | 5/1991 | Pinchuk | |
| 5,092,877 A | 3/1992 | Pinchuk | |
| 5,133,732 A | 7/1992 | Wiktor | |
| 5,226,913 A | 7/1993 | Pinchuk | |
| 5,304,200 A | 4/1994 | Spaulding | |
| 5,314,472 A | 5/1994 | Fontaine | |
| 5,324,472 A | 6/1994 | Page et al. | |
| 5,370,683 A | 12/1994 | Fontaine | |
| 5,443,498 A | 8/1995 | Fontaine | |

(Continued)

FOREIGN PATENT DOCUMENTS

| | | | |
|---|---|---|---|
| DE | 551245 | * | 5/1932 |
| DE | 3041869 A | * | 7/1982 |

(Continued)

*Primary Examiner* — Shelley Self
*Assistant Examiner* — Peter Iannuzzi

(57) ABSTRACT

A method for forming a wave form for a stent includes moving a first forming portion of a first forming member across an axis along which a formable material is provided in a first direction substantially perpendicular to the axis to engage and deform the formable material while engaging the formable material with a first forming portion of the second forming member. The method includes moving the first forming portion of the first forming member and the first forming portion of the second forming member across the axis in a second direction that is substantially opposite the first direction to draw and form the formable material over the first forming portion of the second forming member, disengaging the first forming member from the formable material, and rotating the first forming member to position a second forming portion of the first forming member to face the formable material.

12 Claims, 14 Drawing Sheets

(56) References Cited

U.S. PATENT DOCUMENTS

| | | |
|---|---|---|
| 5,527,354 A | 6/1996 | Fontaine et al. |
| 5,549,663 A | 8/1996 | Cottone, Jr. |
| 5,653,727 A | 8/1997 | Wiktor |
| 5,716,396 A | 2/1998 | Williams, Jr. |
| 5,895,406 A | 4/1999 | Gray et al. |
| 5,902,266 A | 5/1999 | Leone et al. |
| 5,913,897 A | 6/1999 | Corso, Jr. et al. |
| 6,042,597 A | 3/2000 | Kveen et al. |
| 6,117,165 A | 9/2000 | Becker |
| 6,136,023 A | 10/2000 | Boyle |
| 6,190,406 B1 | 2/2001 | Duerig et al. |
| 6,203,569 B1 | 3/2001 | Wijay |
| 6,342,067 B1 | 1/2002 | Mathis et al. |
| 6,355,059 B1 | 3/2002 | Richter et al. |
| 6,423,091 B1 | 7/2002 | Hojeibane |
| 6,432,132 B1 | 8/2002 | Cottone et al. |
| 6,447,540 B1 | 9/2002 | Fontaine et al. |
| 6,503,270 B1 | 1/2003 | Richter et al. |
| 6,610,086 B1 | 8/2003 | Kock et al. |
| 6,656,219 B1 | 12/2003 | Wiktor |
| 6,730,117 B1 | 5/2004 | Tseng et al. |
| 6,736,844 B1 | 5/2004 | Glatt et al. |
| 6,878,162 B2 | 4/2005 | Bales et al. |
| 6,923,828 B1 | 8/2005 | Wiktor |
| 6,969,402 B2 | 11/2005 | Bales et al. |
| 7,004,968 B2 | 2/2006 | Lootz et al. |
| 7,108,714 B1 | 9/2006 | Becker |
| 7,169,175 B2 | 1/2007 | Cottone, Jr. et al. |
| 7,329,277 B2 | 2/2008 | Addonizio et al. |
| 2002/0095208 A1 | 7/2002 | Gregorich et al. |
| 2003/0083736 A1 | 5/2003 | Brown et al. |
| 2004/0044401 A1 | 3/2004 | Bales et al. |
| 2004/0143318 A1 | 7/2004 | Tseng et al. |
| 2005/0085899 A1 * | 4/2005 | Thornton ............ 623/1.16 |
| 2006/0030934 A1 | 2/2006 | Hogendijk et al. |
| 2006/0079955 A1 | 4/2006 | Brown |
| 2008/0097580 A1 | 4/2008 | Dave |
| 2008/0097582 A1 | 4/2008 | Shanley et al. |
| 2008/0183273 A1 | 7/2008 | Mesana et al. |
| 2008/0288053 A1 | 11/2008 | Addonizio et al. |
| 2008/0289389 A1 | 11/2008 | Fitch et al. |
| 2008/0294241 A1 | 11/2008 | Addonizio et al. |
| 2008/0306583 A1 | 12/2008 | Bashiri et al. |
| 2008/0319529 A1 | 12/2008 | Krivoruchko et al. |
| 2008/0319534 A1 | 12/2008 | Birdsall et al. |
| 2008/0319535 A1 | 12/2008 | Craven et al. |
| 2009/0005848 A1 | 1/2009 | Strauss et al. |
| 2009/0024207 A1 | 1/2009 | Addonizio et al. |
| 2009/0036976 A1 | 2/2009 | Beach et al. |
| 2010/0269950 A1 * | 10/2010 | Hoff et al. ............ 140/123 |
| 2011/0067471 A1 * | 3/2011 | Griswold ............ 72/135 |
| 2011/0071620 A1 * | 3/2011 | Bliss et al. ............ 623/1.16 |
| 2012/0018496 A1 | 1/2012 | Carmody et al. |

FOREIGN PATENT DOCUMENTS

| | | |
|---|---|---|
| EP | 007148 A1 * | 1/1980 |
| EP | 945107 | 9/1999 |
| EP | 1155664 | 11/2007 |
| GB | 2281865 | 3/1995 |
| WO | WO2007/080611 | 7/2007 |
| WO | WO2007/095466 | 8/2007 |
| WO | WO2008/028964 | 3/2008 |
| WO | WO2008/100783 | 8/2008 |
| WO | WO2011/034793 | 3/2011 |

* cited by examiner

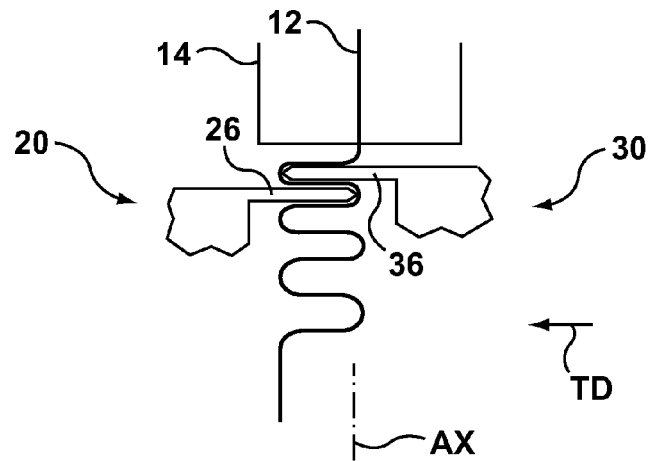
FIG. 19
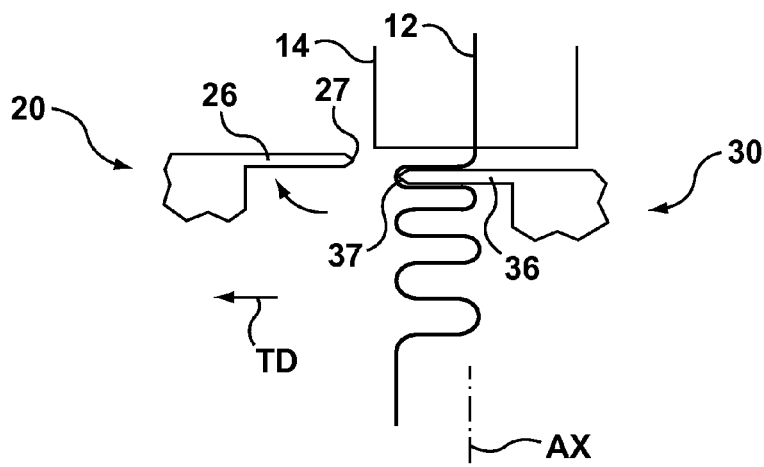
FIG. 20
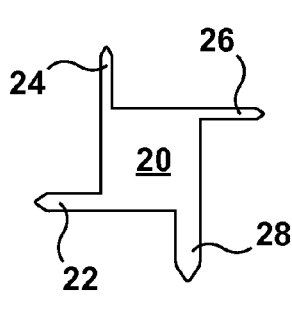 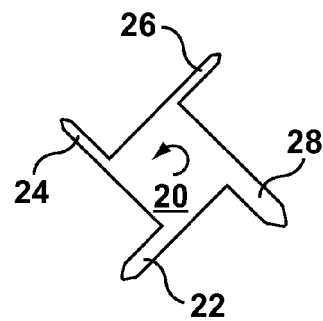 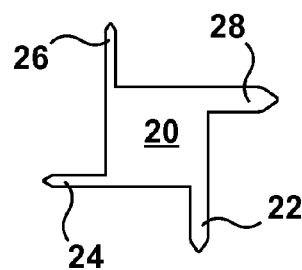
FIG. 21A   FIG. 21B   FIG. 21C

METHOD AND APPARATUS FOR CREATING FORMED ELEMENTS USED TO MAKE WOUND STENTS

BACKGROUND OF THE INVENTION

1. Field of the Invention

The present invention is generally related to an apparatus and method for forming a wave form for a stent. More particularly, the present invention is related to an apparatus and method for forming the wave form from a formable material, such as a wire or a strip of material.

2. Background of the Invention

A stent is typically a hollow, generally cylindrical device that is deployed in a body lumen from a radially contracted configuration into a radially expanded configuration, which allows it to contact and support a vessel wall. A plastically deformable stent can be implanted during an angioplasty procedure by using a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s) or strip(s) of material, may be cut from a tube, or may be cut from a sheet of material and then rolled into a tube-like structure. While some stents may include a plurality of connected rings that are substantially parallel to each other and are oriented substantially perpendicular to a longitudinal axis of the stent, others may include a helical coil that is wrapped or wound around a mandrel aligned with the longitudinal axis at a non-perpendicular angle.

Stent designs that are comprised of wound materials generally have complex geometries so that the final stents may be precisely formed. The small size and complexity of some stent designs generally makes its formation difficult. Wound stents are formed such that when unsupported, they create the desired stent pattern and vessel support. This process generally involves winding a source material around a supporting structure such as a rod or mandrel and creating a helical or spring-like wrap pattern. To provide greater support, along this wrapped element, geometries are formed into the source material to better support the tissue in between each wrap, usually of sinusoidal nature. A potential down side to a wrapped stent is that the ends of the stent are generally not perpendicular to the longitudinal axis of the stent, but rather terminate at a pitch angle induced by the helical wrapping.

SUMMARY OF THE INVENTION

Embodiments of the present invention describe an apparatus and method for forming a wave form for a stent that provides formed geometries that can alter a pitch angle such that the wound stent terminates at a substantially perpendicular angle to the longitudinal axis of the stent. More specifically, the apparatus and method according to embodiments of the present invention allow for the amplitude and wavelength of any individual or half element of the wave form to be manipulated to provide the desired interwrap support.

According to an aspect of the present invention, there is provided a method for forming a wave form for a stent. The method includes providing a length of a formable material from a supply of the formable material in a feeder along an axis in a first direction in between a first forming member and a second forming member. The second forming member is positioned closer to the feeder than the first forming member. The method also includes moving a first forming portion of the first forming member across the axis in a second direction substantially perpendicular to the first direction to engage and deform the formable material while engaging the formable material with a first forming portion of the second forming member, moving the first forming portion of the first forming member and the first forming portion of the second forming member across the axis in a third direction that is substantially opposite the second direction to draw and form the formable material over the first forming portion of the second forming member, disengaging the first forming member from the formable material, and rotating the first forming member. The method further includes moving the first forming member and the second forming member relative to each other so that the first forming member is positioned closer to the feeder than the second forming member, moving a second forming portion of the first forming member into engagement with the formable material, and moving the second forming portion of the first forming member and the first forming portion of the second forming member across the axis in the second direction to draw and form the formable material over the second forming portion of the first forming member.

According to an aspect of the present invention, there is provided a forming apparatus configured to form a wave form for a stent out of a formable material. The wave form includes a plurality of substantially straight portions and a plurality of curved portions. The apparatus includes a feeder constructed and arranged to receive a supply of the formable material and to provide the formable material along an axis, and a first forming member configured to be movable along two orthogonal axes and rotatable in a plane defined by the two orthogonal axes. The first forming member includes a first forming portion and a second forming portion having a shape different from the first forming portion. Each of the first forming portion and the second forming portion is configured to engage and deform the formable material. The apparatus also includes a second forming member positioned on an opposite side of the axis relative to the first forming member. The second forming member is configured to be movable along the two orthogonal axes and comprising a first forming portion configured to engage and deform the formable material. The apparatus also includes a controller in communication with the feeder, the first forming member, and the second forming member. The controller is configured to control movement of the first and second forming members to form the wave form.

According to an aspect of the present invention, there is provided a method for forming a wave form for a stent. The method includes providing a length of a formable material from a supply of the formable material in a feeder along an axis in a first direction in between a first forming member and a second forming member, the second forming member being positioned closer to the feeder than the first forming member. The method includes moving a first forming portion of the first forming member into contact with the formable material and across the axis in a second direction substantially perpendicular to the first direction, and folding the formable material over a first forming portion of the second forming member by moving the second forming member and the first forming member in a third direction substantially opposite the second direction and moving the second forming member and the first forming member in a fourth direction substantially opposite the first direction. The method includes disengaging the first forming member from the formable material, rotating the first forming member, and moving a second forming portion of the first forming member into engagement with the formable material at a position closer to the feeder than the second forming member. The method includes drawing a length of the formable member from the feeder with the first forming member and the second forming member, and folding the formable material over the second forming portion of the first member by moving the first forming member and the second forming member in the second direction and moving the first forming member and the second forming member in the fourth direction.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 19 is a schematic view of the forming apparatus of FIG. 18, with the first forming member and the second forming member being moved in the third direction to deform the formable material into another half element of the wave form;

FIG. 20 is a schematic view of the forming apparatus of FIG. 19, with the first forming member moving away from the formable material and towards the feeder; and FIGS. 21A-C are schematic views of the first forming member being rotated 90°;

FIGS. 25A-C are schematic views of the second forming member being rotated 90°;

DETAILED DESCRIPTION OF EMBODIMENTS OF THE INVENTION

The following detailed description is merely exemplary in nature and is not intended to limit the invention or the application and use of the invention. Furthermore, there is no intention to be bound by any expressed or implied theory presented in the preceding technical field, background, brief summary or the following detailed description.

Figure 1:
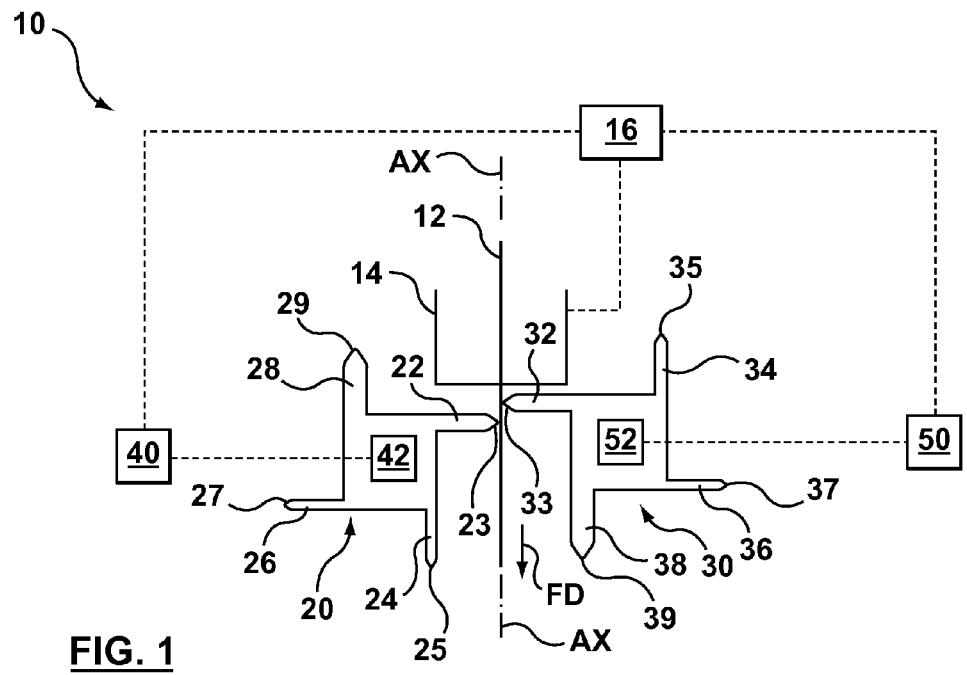
FIG. 1 is a schematic view of an embodiment of a forming apparatus configured to deform a formable material into a desired wave form for a stent, with the formable material being provided in a first direction by a feeder.

FIG. 1 schematically illustrates an embodiment of a forming apparatus 10 that is configured to deform a formable material 12 into a desired shape, i.e. wave form, as discussed in further detail below. The forming apparatus 10 includes a feeder 14 that is constructed and arranged to receive a supply of the formable material and to provide the formable material 12 substantially along an axis AX in a first direction FD. The feeder 14 may be configured to actively feed the formable material 12 along the axis AX in the first direction, or may be configured to passively feed the formable material by allowing the formable material 12 to be drawn from the feeder 14, as discussed in further detail below. The forming apparatus 10 also includes a controller 16 that is configured to communicate with the feeder 14. The controller 16 may be programmed to provide signals to the feeder 14 so that the feeder 14 feeds the formable material 12 at a desired rate or velocity, and also stops feeding the formable material 12 when desired.

The forming apparatus 10 also includes a first forming member 20 and a second forming member 30. The first forming member 20 includes a first forming portion 22 that has a first engaging surface 23 at a distal end thereof, a second forming portion 24 that has a second engaging surface 25 at a distal end thereof, a third forming portion 26 that has a third engaging surface 27 at a distal end thereof, and a fourth forming portion 28 that has a fourth engaging surface 29 at a distal end thereof. The engaging surfaces 23, 25, 27, 29 are configured to engage the formable material 12 on one side thereof and deform the formable material 12 into a desired shape, as discussed in further detail below. Each of the forming portions 22, 24, 26, 28 may generally be elongated or finger-like in shape, as illustrated, but the illustrated embodiments should not be considered to be limiting in any way.

Similar to the first forming member 20, the second forming member 30 includes a first forming portion 32 that has a first engaging surface 33 at a distal end thereof, a second forming portion 34 that has a second engaging surface 35 at a distal end thereof, a third forming portion 36 that has a third engaging surface 37 at a distal end thereof, and a fourth forming portion 38 that has a fourth engaging surface 39 at a distal end thereof. The engaging surfaces 33, 35, 37, 39 are configured to engage the formable material 12 on one side thereof and deform the formable material 12 into a desired shape, as discussed in further detail below. Each of the forming portions 32, 34, 36, 38 may generally be elongated or finger-like in shape, as illustrated, but the illustrated embodiments should not be considered to be limiting in any way.

As illustrated in FIG. 1, the first forming member 20 and the second forming member 30 are positioned so that the first engaging surface 23 of the first forming member 20 and the first engaging surface 33 of the second forming member 30 face each other on opposite sides of the formable material 12.

The first forming member 20 and the second forming member 30 may be moved relative to the feeder 14 by actuators 40, 50, respectively, that are schematically illustrated in FIG. 1. Each of the actuators 40, 50 is in communication with the controller 16 so that the controller 16 may send signals to the actuators 40, 50 to control movement of the first and second forming members 20, 30, respectively. A suitable motor or actuator 42 that is in communication with the controller 16 may be used to rotate the first forming member 20, and a suitable motor or actuator 52 that is in communication with the controller 16 may be used to rotate the second forming member 30. In addition, the feeder 14 may be connected to an actuator (not shown) that is in communication with the controller 16 so that the controller may control movement of the feeder 14 relative to the first and second forming members 20, 30.

In operation, the first forming member 20 is initially positioned on one side of the axis AX, and the second forming member 30 is initially positioned on the opposite side of the axis AX relative to the first forming member 20 such that the first engaging surface 23 of the first forming member 20 and the first engaging surface 33 of the second forming member 30 face each other, as illustrated in FIG. 1. In an embodiment, the controller 16 sends a signal to the feeder 14 to advance the formable material 12 by a predetermined amount or length in the first direction FD substantially along the axis AX. In an embodiment, the feeder 14 does not actively advance the formable material 12, but instead allows the formable material 12 to be drawn by the first forming member 20 and/or the second forming member 30, as understood by one of ordinary skill in the art.

Figure 2:
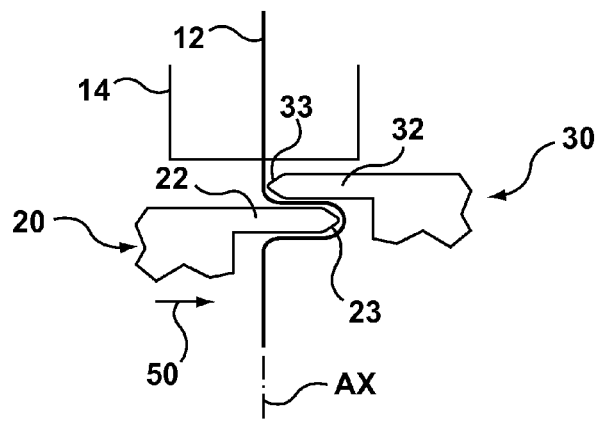
FIG. 2 is a schematic view of the forming apparatus of FIG. 1, with a first forming member being moved in a second direction substantially perpendicular to the first direction to deform the formable material into a half element of the wave form.

As illustrated in FIG. 2, the first forming member 20 is moved in a second direction SD that is substantially perpendicular to the first direction FD and the axis AX so that the first engaging surface 23 engages the formable material 12 and deforms the formable material 12 as the first engaging surface 23 passes over the axis AX. The second forming member 30 may hold its position relative to the axis AX until the first forming member 20 has completed its movement in the first direction FD.

Figure 3:
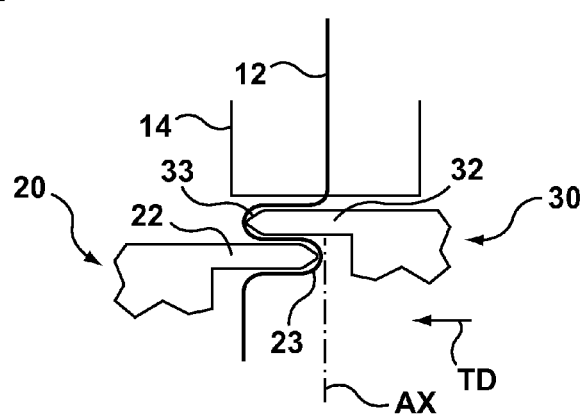
FIG. 3 is a schematic view of the forming apparatus of FIG. 2, with a second forming member and the first forming member being moved in a third direction substantially opposite the second direction to deform the formable material into another half element of the wave form.

FIG. 3 illustrates the second forming member 30 engaging the formable material 12 with the first engaging surface 33 and moving in a third direction TD that is substantially opposite the second direction SD and substantially perpendicular to the axis AX. At the same time or at about the same time, the first forming member 20 also moves with the second forming member 30 in the third direction TD while still engaging the formable material 12, and the feeder 14 feeds an additional amount of formable material 12 in the first direction FD or the feeder 14 allows the additional amount of formable material 12 to be drawn in the first direction FD. Due to the movement of the first and second forming members 20, 30, the formable material 12 folds over the top of the first elongated portion 32 of the second forming member 30, as illustrated in FIG. 3, to form a half element (i.e., half wavelength) of the wave form.

Figure 4:
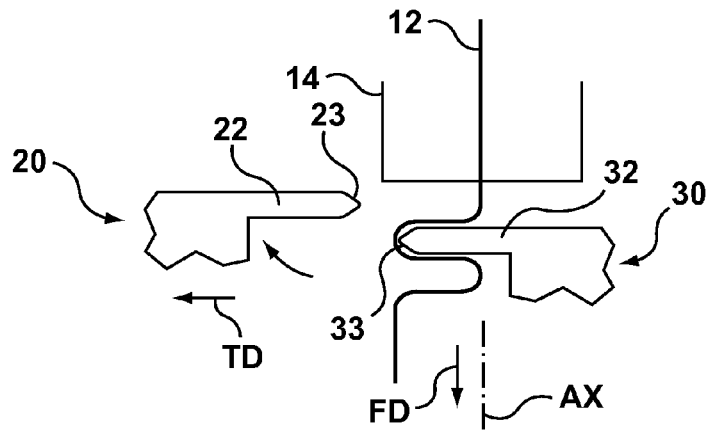
FIG. 4 is a schematic view of the forming apparatus of FIG. 3, with the first forming member moving away from the formable material and towards the feeder.

As illustrated in FIG. 4, the first forming member 20 then disengages from the formable material 12 and moves away from the formable material 12 in the third direction TD. In addition, the first forming member 20 moves towards the feeder 14 in a direction that is substantially opposite the first direction FD. At the same time, or about the same time, the second forming member 30 moves in the first direction FD as the feeder 14 provides a small amount of formable material 12 in the first direction FD, desirably at about the same rate that the second forming member 30 moves in the first direction FD, to make room for the first forming member 20 in between the feeder 14 and the second forming member 30. The formable material 12 may be drawn from the feeder 14 or the feeder 14 may actively feed the formable material 12.

Figure 5A:
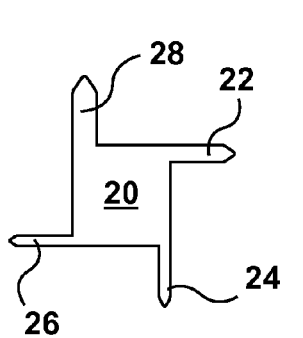
FIGS. 5A-C are schematic views of the first forming member being rotated 90°.
Figure 5B:
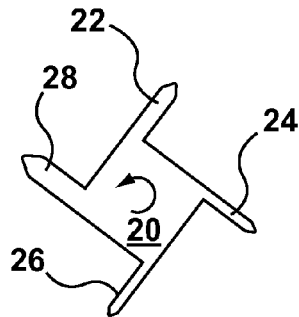
Figure 5C:
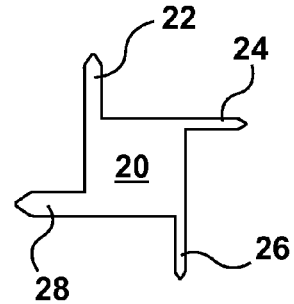

FIGS. 5A-C illustrate the rotation of the first forming member 20 about 90° from its orientation illustrated in FIGS. 1-4. In the illustrated embodiment, the first forming member 20 is rotated in a counterclockwise direction. In an embodiment, the first forming member 20 may be rotated in a clockwise direction. Also, in an embodiment, the first forming member 20 may be rotated about 180°. The illustrated embodiment is not intended to be limiting in any way.

Figure 6:
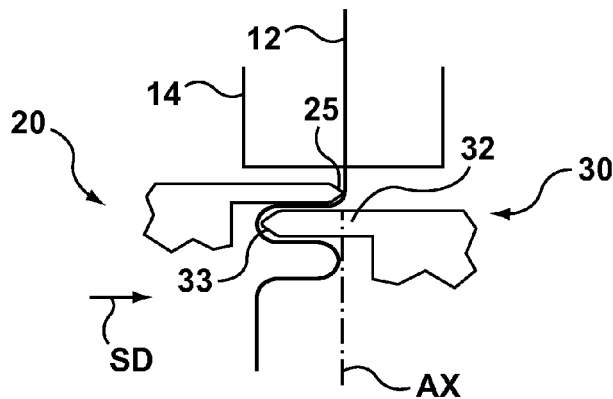
FIG. 6 is a schematic view of the forming apparatus of FIG. 4, with the first forming member, after being rotated 90°, being moved towards the formable material in the second direction.
Figure 7:
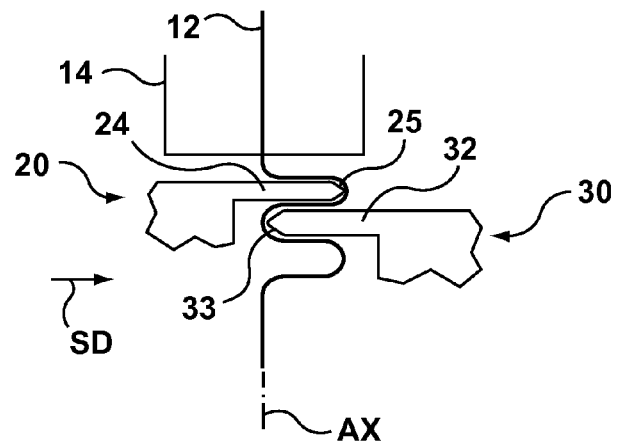
FIG. 7 is a schematic view of the forming apparatus of FIG. 6, with the first forming member and the second forming member being moved in the second direction to deform the formable material into another half element of the wave form.

The first forming member 20 then moves in the second direction SD towards the formable material 12, engages the formable material 12 with the second engaging surface 25, as illustrated in FIG. 6, and continues to move in the second direction SD, as illustrated in FIG. 7. At the same time, or about the same time, that the second engaging surface 25 of the first forming member 20 moves across the axis AX and to the position illustrated in FIG. 7, an additional length of the formable material 12 is provided to accommodate for the distance traveled by the second engaging surface 25 relative to the axis AX, and the second forming member 30 moves at substantially the same speed as the first forming member 20, in the second direction SD. The additional length may be drawn from the feeder 14 or may be fed by the feeder 14, as discussed above.

Figure 8:
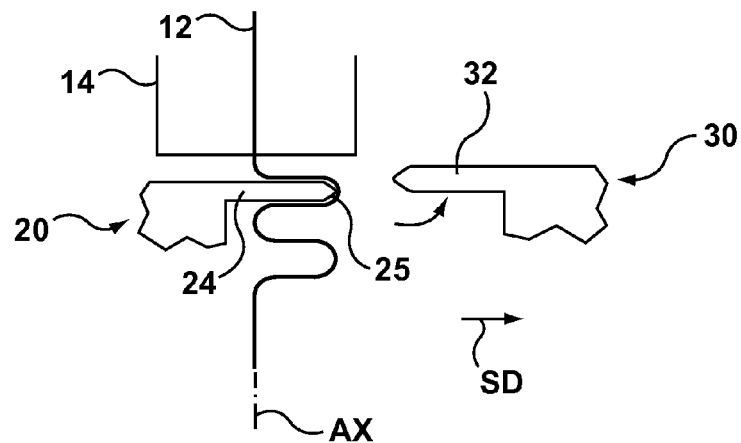
FIG. 8 is a schematic view of the forming apparatus of FIG. 7, with the second forming member moving away from the formable material and towards the feeder.

Similar to the movement of the first forming member 20 that is represented in FIG. 4, the second forming member 30 then moves away from the formable material 12 and away from the axis AX in the second direction SD, and also moves towards the feeder 14 in a direction substantially opposite the first direction, as illustrated in FIG. 8. At the same time, or about the same time, the first forming member 20 moves substantially in the first direction FD as a small amount of formable material is provided in the first direction along the axis AX so as to make room for the second forming member 30 in between the feeder 14 and the first forming member 20.

Figures 9A, 9B, 9C:
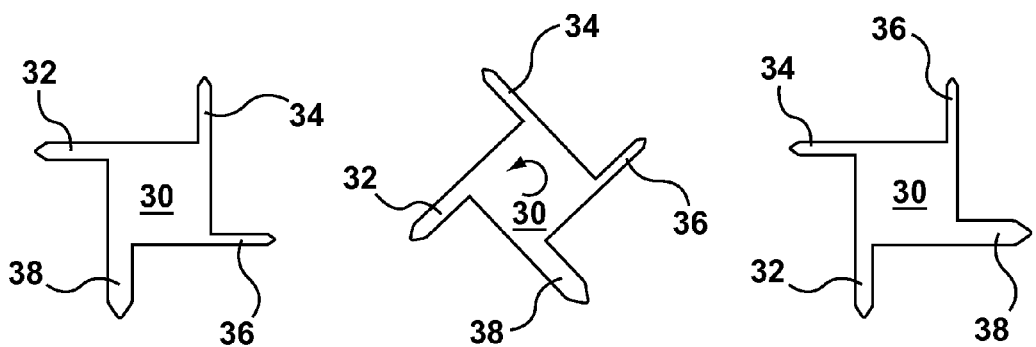
FIGS. 9A-9C are schematic views of the second forming member being rotated 90°.

FIGS. 9A-C illustrate the rotation of the second forming member 30 about 90° from its orientation illustrated in FIGS. 1-4 and 6-8. In the illustrated embodiment, the second forming member 30 is rotated in a counterclockwise direction. In an embodiment, the second forming member 30 may be rotated in a clockwise direction. Also, in an embodiment, the second forming member 30 may be rotated about 180°. The illustrated embodiment is not intended to be limiting in any way.

Figure 10:
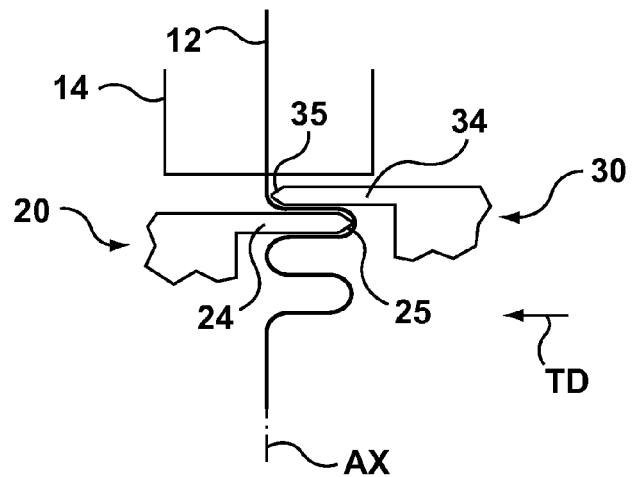
FIG. 10 is a schematic view of the forming apparatus of FIG. 8, with the second forming member, after being rotated 90°, being moved towards the formable material in the third direction.
Figure 11:
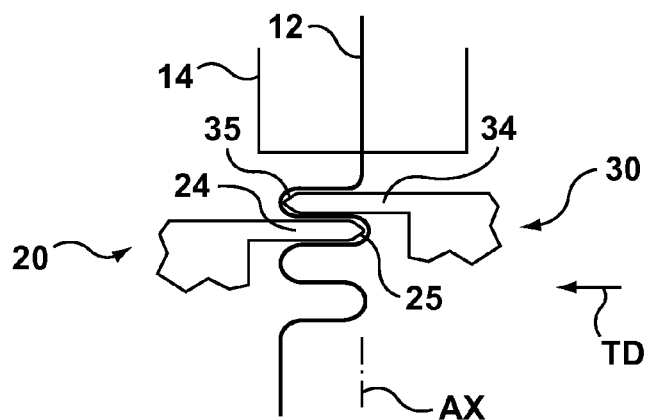
FIG. 11 is a schematic view of the forming apparatus of FIG. 10, with the first forming member and the second forming member being moved in the third direction to deform the formable material into another half element of the wave form.

The second forming member 30 then moves in the third direction TD towards the formable material 12, as illustrated in FIG. 10, engages the formable material 12 with the second engaging surface 35, and continues to move in the third direction TD, as illustrated in FIG. 11. At the same time, or about the same time, that the second engaging surface 35 of the second forming member 30 moves across the axis AX and to the position illustrated in FIG. 11, a suitable length of the formable material 12 is provided (i.e. drawn or fed) to accommodate for the distance traveled by the second engaging surface 35 relative to the axis AX.

Figure 12:
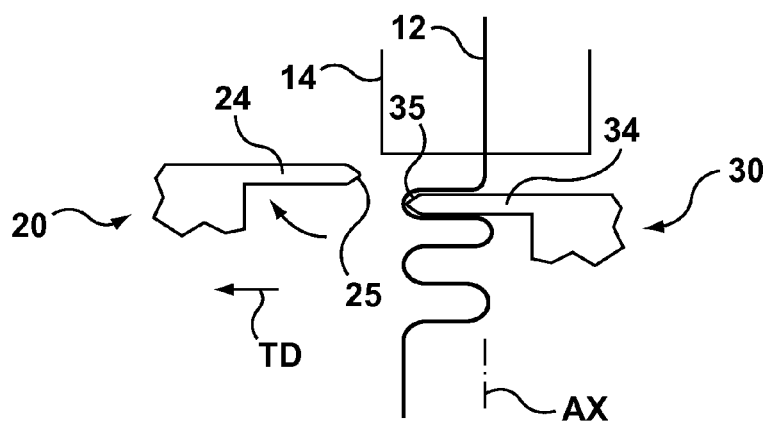
FIG. 12 is a schematic view of the forming apparatus of FIG. 11, with the first forming member moving away from the formable material and towards the feeder.

Similar to the movement of the first forming member 20 illustrated in FIG. 4, the first forming member 20 then disengages from the formable material 12 and moves away from the formable material in the third direction TD, as illustrated in FIG. 12. In addition, the first forming member 20 moves towards the feeder 14 in a direction that is substantially opposite the first direction FD. At the same time, or about the same time, the second forming member 30 moves in the first direction FD as a small amount of formable material 12 is provided in the first direction, desirably at about the same rate that the second forming member 30 moves in the first direction FD, to make room for the first forming member 20 in between the feeder 14 and the second forming member 30.

Figure 13A:
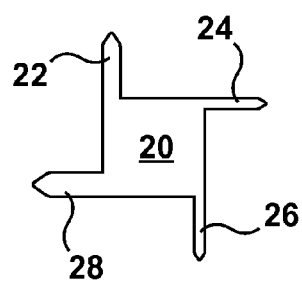
FIGS. 13A-C are schematic views of the first forming member being rotated 90°.
Figure 13B:
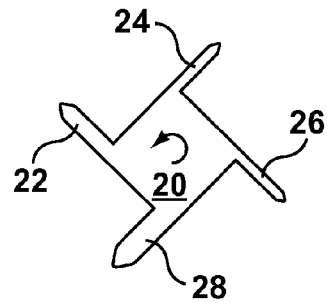
Figure 13C:
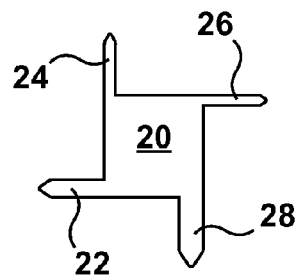

FIGS. 13A-C illustrate the rotation of the first forming member 20 about 90° from its orientation illustrated in FIGS. 6-8 and 10-12 in the counterclockwise direction. As noted above, in other embodiments, the first forming member 20 may be rotated in a clockwise direction and/or may be rotated about 180°. The illustrated embodiment is not intended to be limiting in any way.

Figure 14:
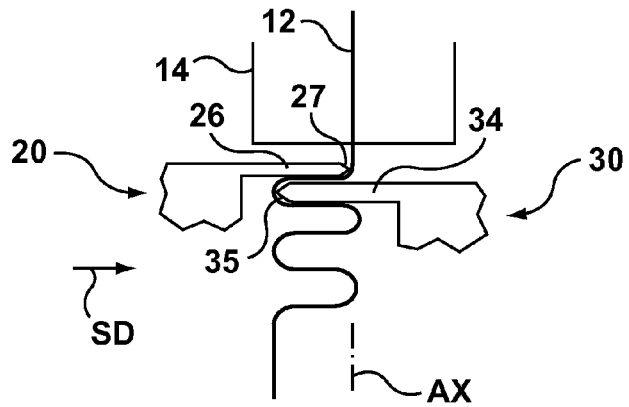
FIG. 14 is a schematic view of the forming apparatus of FIG. 12, with the first forming member, after being rotated 90°, being moved towards the formable material in the second direction.
Figure 15:
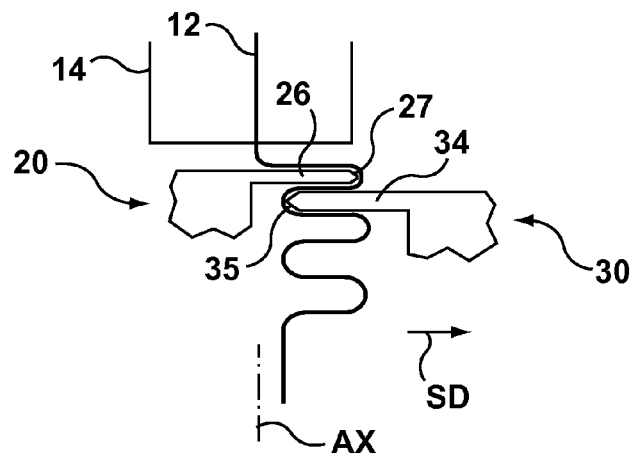
FIG. 15 is a schematic view of the forming apparatus of FIG. 14, with the first forming member and the second forming member being moved in the second direction to deform the formable material into another half element of the wave form.

The first forming member 20 then moves in the second direction SD towards the formable material 12, as illustrated in FIG. 14, engages the formable material 12 with the third engaging surface 27, and continues to move in the second direction SD, as illustrated in FIG. 15. At the same time, or about the same time, that the third engaging surface 27 of the first forming member 20 moves across the axis AX and to the position illustrated in FIG. 15, a suitable length of the formable material 12 is provided to accommodate for the distance traveled by the third engaging surface 27 relative to the axis AX.

Figure 16:
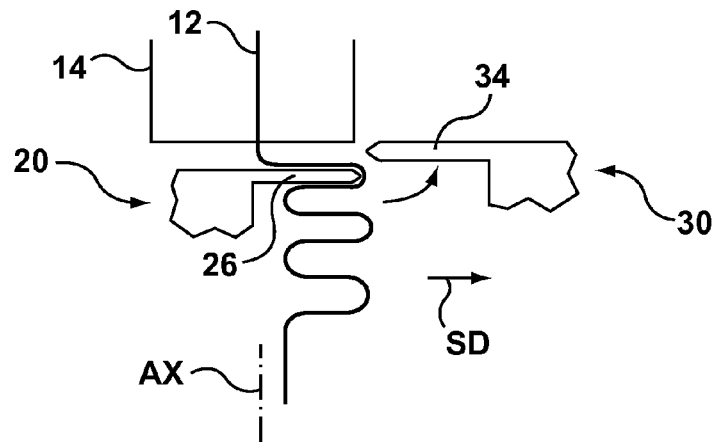
FIG. 16 is a schematic view of the forming apparatus of FIG. 15, with the second forming member moving away from the formable material and towards the feeder.

Similar to the movement of the second forming member 30 that is represented in FIG. 7, the second forming member 30 then moves away from the formable material 12 and away from the axis AX in the second direction SD, and also moves towards the feeder 14 in a direction substantially opposite the first direction, as illustrated in FIG. 16. At the same time, or about the same time, the first forming member 20 moves substantially in the first direction FD and a small amount of formable material is provided in the first direction along the axis AX so as to make room for the second forming member 30 in between the feeder 14 and the first forming member 20.

Figures 17A, 17B, 17C:
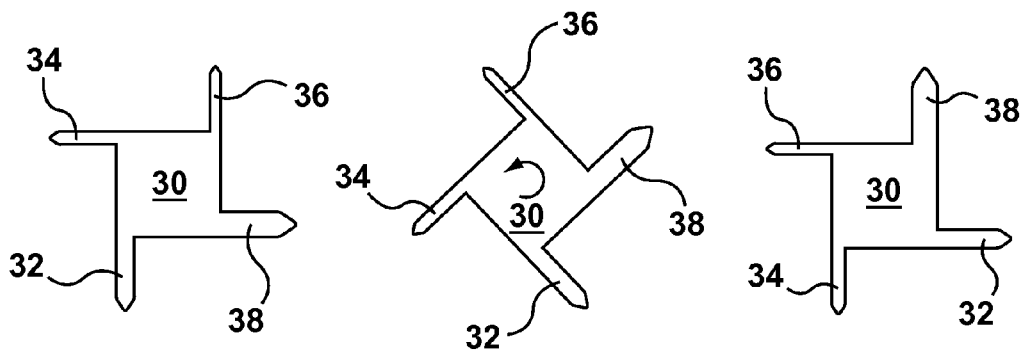
FIGS. 17A-17C are schematic views of the second forming member being rotated 90°.

FIGS. 17A-C illustrate the rotation of the second forming member 30 in the counterclockwise direction about 90° from its orientation illustrated in FIGS. 10-12 and 14-16. As noted above, in other embodiments, the second forming member 30 may be rotated in a clockwise direction and/or may be rotated about 180°. The illustrated embodiment is not intended to be limiting in any way.

Figure 18:
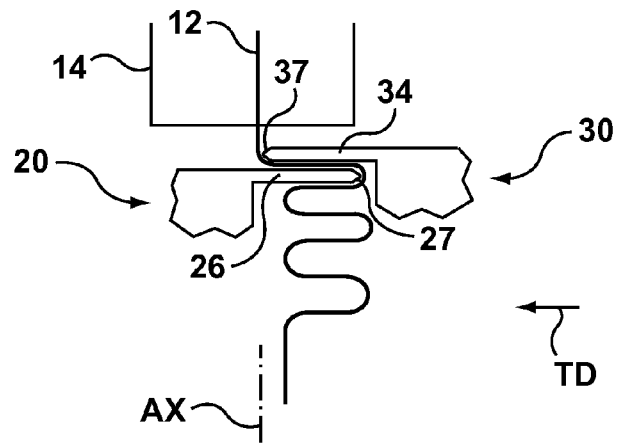
FIG. 18 is a schematic view of the forming apparatus of FIG. 16, with the second forming member, after being rotated 90°, being moved towards the formable material in the third direction.

The second forming member 30 then moves in the third direction TD towards the formable material 12, as illustrated in FIG. 18, engages the formable material 12 with the third engaging surface 37, and continues to move in the third direction TD, as illustrated in FIG. 19. At the same time, or about the same time, that the third engaging surface 37 of the first forming member 30 moves across the axis AX and to the position illustrated in FIG. 19, the feeder 14 feeds a suitable length of the formable material 12 to accommodate for the distance traveled by the third engaging surface 37 relative to the axis AX.

Similar to the movement of the first forming member 20 illustrated in FIG. 4, the first forming member 20 then disengages from the formable material 12 and moves away from the formable material in the third direction TD, as illustrated in FIG. 20. In addition, the first forming member 20 moves towards the feeder 14 in a direction that is substantially opposite the first direction FD. At the same time, or about the same time, the second forming member 30 moves in the first direction FD as a small amount of formable material 12 is provided in the first direction, desirably at about the same rate that the second forming member 30 moves in the first direction FD, to make room for the first forming member 20 in between the feeder 14 and the second forming member 30.

FIGS. 21A-C illustrate the rotation of the first forming member 20 about 90° from its orientation illustrated in FIGS. 14-16 and 18-20 in the counterclockwise direction. As noted above, in other embodiments, the first forming member 20 may be rotated in a clockwise direction and/or may be rotated about 180°. The illustrated embodiment is not intended to be limiting in any way.

Figure 22:
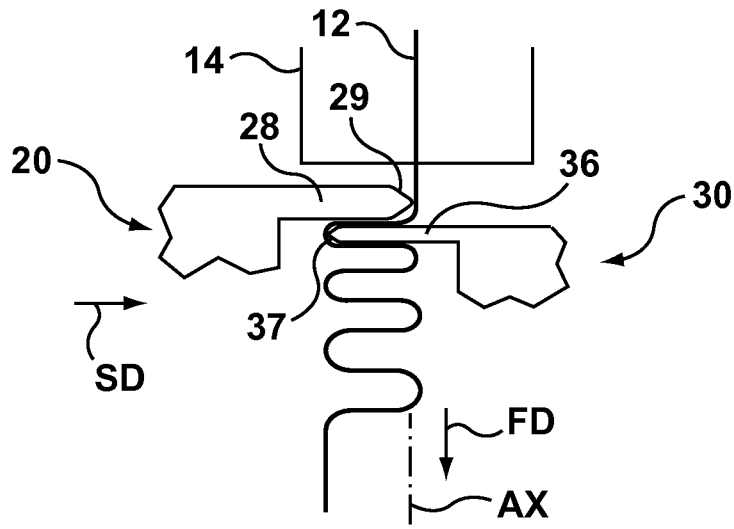
FIG. 22 is a schematic view of the forming apparatus of FIG. 20, with the first forming member, after being rotated 90°, being moved towards the formable material in the second direction.
Figure 23:
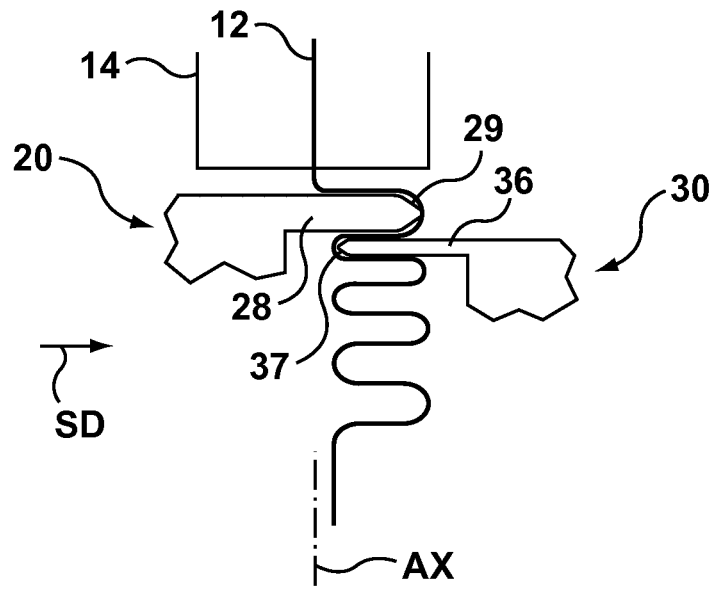
FIG. 23 is a schematic view of the forming apparatus of FIG. 22, with the first forming member and the second forming member being moved in the second direction to deform the formable material into another half element of the wave form.

The first forming member 20 then moves in the second direction SD towards the formable material 12, as illustrated in FIG. 22, engages the formable material 12 with the fourth engaging surface 29, and continues to move in the second direction SD, as illustrated in FIG. 23. At the same time, or about the same time, that the fourth engaging surface 29 of the first forming member 20 moves across the axis AX and to the position illustrated in FIG. 23, a suitable length of the formable material 12 is provided to accommodate for the distance traveled by the fourth engaging surface 29 relative to the axis AX.

Figure 24:
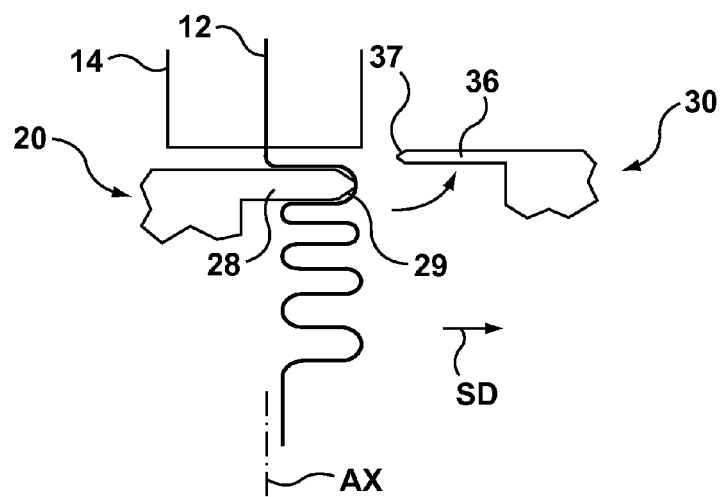
FIG. 24 is a schematic view of the forming apparatus of FIG. 23, with the second forming member moving away from the formable material and towards the feeder.

Similar to the movement of the second forming member 30 that is represented in FIG. 7, the second forming member 30 then moves away from the formable material 12 and away from the axis AX in the second direction SD, and also moves towards the feeder 14 in a direction substantially opposite the first direction, as illustrated in FIG. 24. At the same time, or about the same time, the first forming member 20 moves substantially in the first direction FD and a small amount of formable material is provided in the first direction along the axis AX so as to make room for the second forming member 30 in between the feeder 14 and the first forming member 20.

Figure 25B:
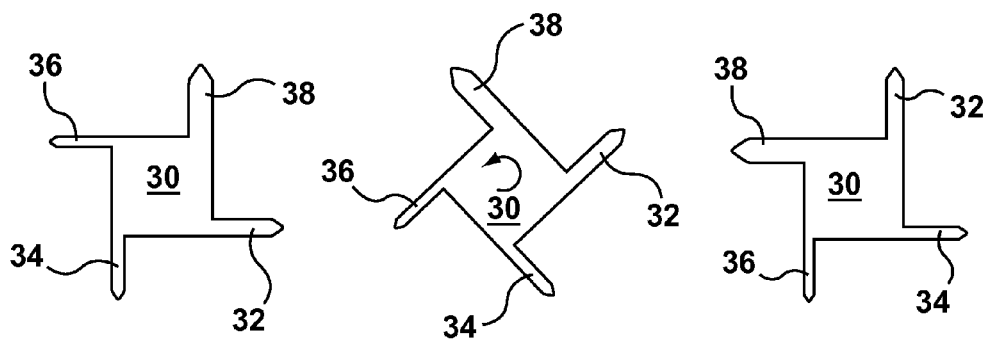

FIGS. 25A-C illustrate the rotation of the second forming member 30 in the counterclockwise direction about 90° from its orientation illustrated in FIGS. 18-20 and 22-24. As noted above, in other embodiments, the second forming member 30 may be rotated in a clockwise direction and/or may be rotated about 180°. The illustrated embodiment is not intended to be limiting in any way.

Figure 26:
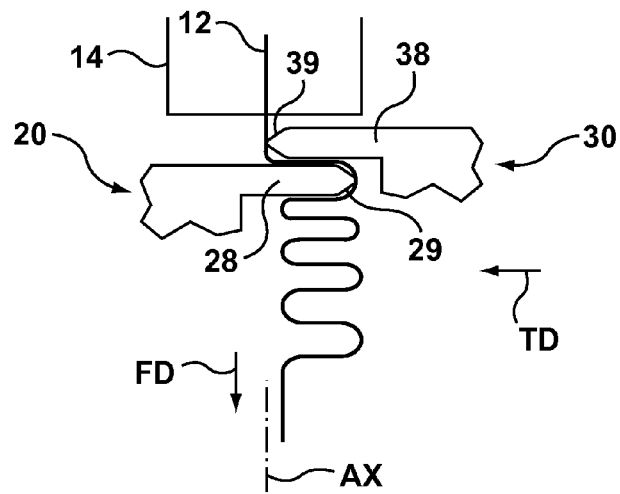
FIG. 26 is a schematic view of the forming apparatus of FIG. 24, with the second forming member, after being rotated 90°, being moved towards the formable material in the third direction.
Figure 27:
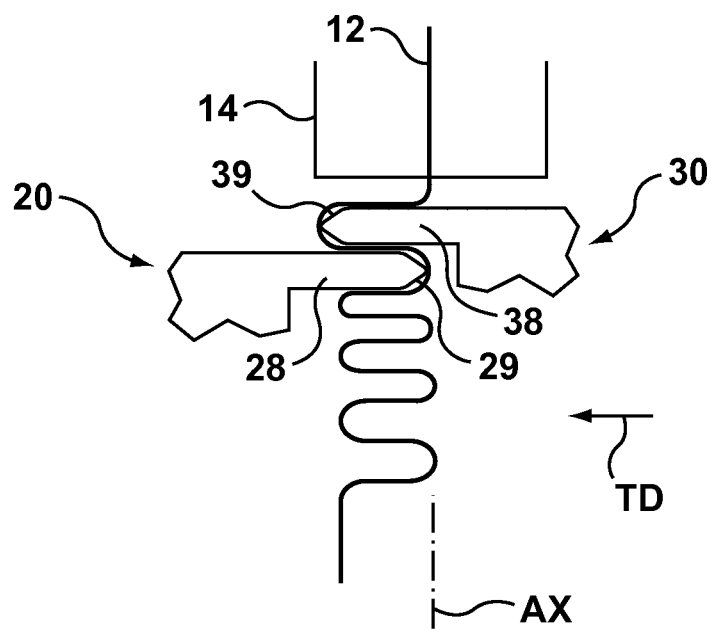
FIG. 27 is a schematic view of the forming apparatus of FIG. 26, with the first forming member and the second forming member being moved in the third direction to deform the formable material into another half element of the wave form.

The second forming member 30 then moves in the third direction TD towards the formable material 12, as illustrated in FIG. 26, engages the formable material 12 with the fourth engaging surface 39, and continues to move in the third direction TD, as illustrated in FIG. 27. At the same time, or about the same time, that the fourth engaging surface 39 of the first forming member 30 moves across the axis AX and to the position illustrated in FIG. 27, the feeder 14 feeds a suitable length of the formable material 12 to accommodate for the distance traveled by the fourth engaging surface 39 relative to the axis AX.

Figure 28:
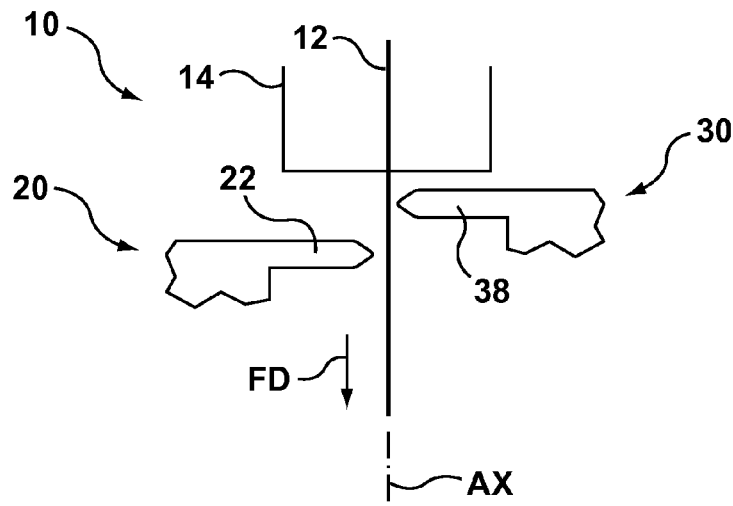
FIG. 28 is a schematic view of an embodiment of the forming apparatus of FIG. 1, with the formable material being provided in the first direction.
Figure 29:
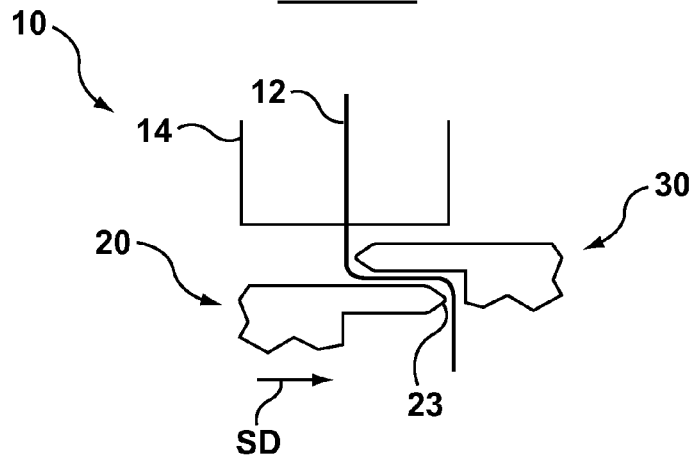
FIG. 29 is a schematic view of the forming apparatus of FIG. 28, with the first forming member being moved in the second direction to deform the formable material.

FIGS. 28-36 illustrate another embodiment of a method of forming a wave form in accordance with another embodiment of the present invention. As illustrated in FIG. 28, the method starts with providing a length of the formable material 12 in between the first forming member 20 and the second forming member 30 in the first direction FD. FIG. 29 illustrates the first forming member 20 being moved in the second direction SD so that the first engaging surface 23 engages the formable material 12 and deforms the formable material 12 while the second forming member 30 remains stationary.

Figure 30:
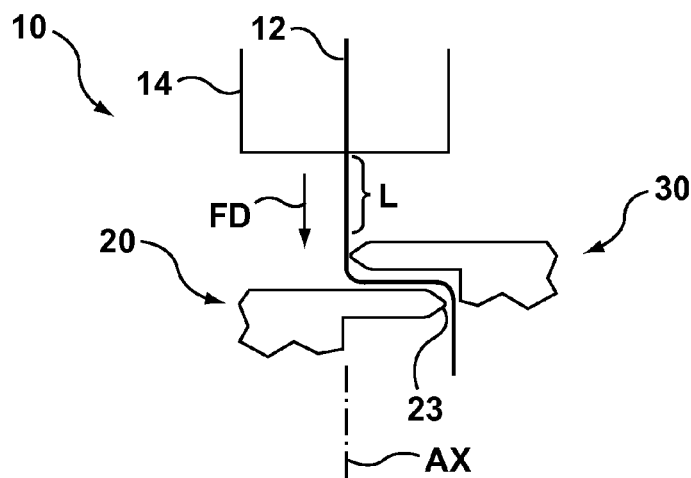
FIG. 30 is a schematic view of the forming apparatus of FIG. 29, with the formable material being drawn from the feeder in the first direction by movement of the first forming member and the second forming member.
Figure 31:
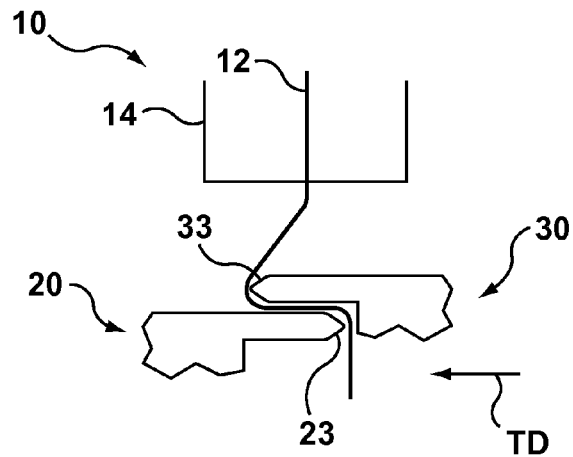
FIG. 31 is a schematic view of the forming apparatus of FIG. 30, with the first forming member and the second forming member being moved in the third direction.
Figure 32:
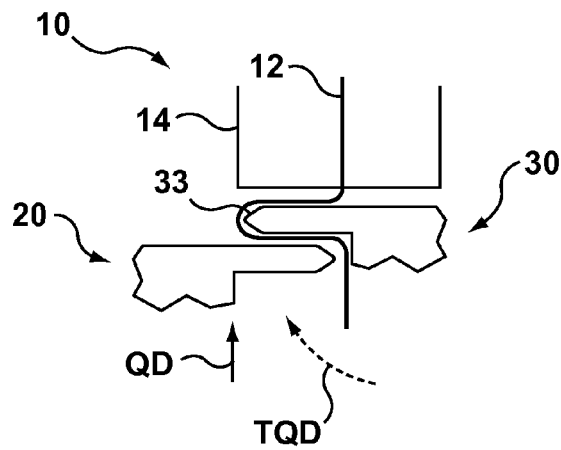
FIG. 32 is a schematic view of the forming apparatus of FIG. 31, with the first forming member and the second forming member being moved in a fourth direction, which is opposite the first direction.

As illustrated in FIG. 30, the first forming member 20 and the second forming member 30 are moved in the first direction so that a length L of the formable material may be drawn out of the feeder 14. The length L should be greater than or equal to the desired length of next strut of the wave form. As illustrated in FIG. 31, the first forming member 20 and the second forming member 30 are moved in the third direction TD as the first engaging surfaces 23, 33 engage the formable material 12. The first forming member 20 and the second forming member 30 are also moved in a fourth direction QD that is opposite the first direction, as illustrated in FIG. 32. In an embodiment, rather than the first forming member 20 and the second forming member 30 being moved in the second direction SD and the fourth direction QD sequentially, the first forming member 20 and the second forming member 30 may be moved along an arc or trajectory, as indicated by the dashed line TQD in FIG. 32.

Figure 33:
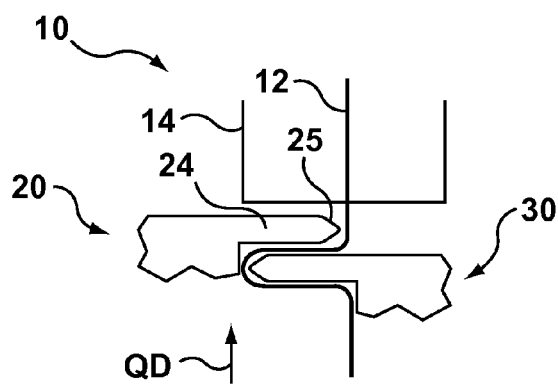
FIG. 33 is a schematic view of the forming apparatus of FIG. 32, after the first forming member has been moved to a position in between the feeder and the second forming member.
Figure 34:
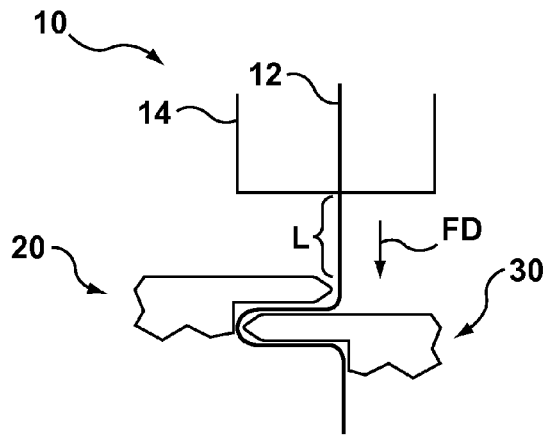
FIG. 34 is a schematic view of the forming apparatus of FIG. 33, with the formable material being drawn in the first direction by movement of the first forming member and the second forming member.

After the portion of the wave form has been formed, as illustrated in FIG. 32, the first forming member 20 is moved in the fourth direction QD to a position that is in between the second forming member 30 and the feeder 14, as illustrated in FIG. 33. In addition, the first forming member 20 may be rotated, as illustrated in FIGS. 5A-C. With the first forming member 20 in this position, the first forming member 20 and the second forming member 30 may be moved in the first direction FD so that the formable material 12 may be drawn in the first direction by a length L, as illustrated in FIG. 34. As before, the length L is greater than or equal to the desired length of the next strut of the wave form.

Figure 35:
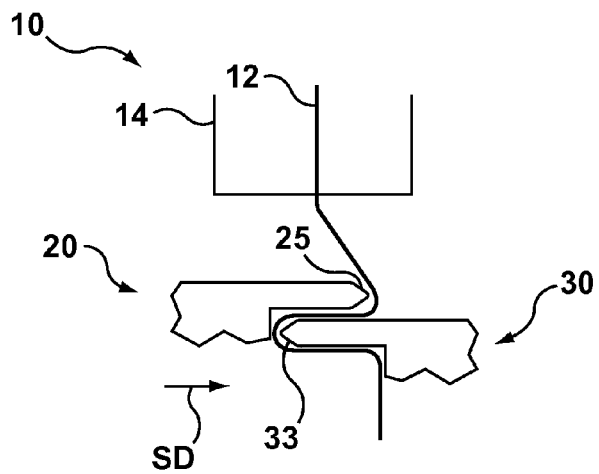
FIG. 35 is a schematic view of the forming apparatus of FIG. 34, with the first forming member and the second forming member being moved in the second direction.
Figure 36:
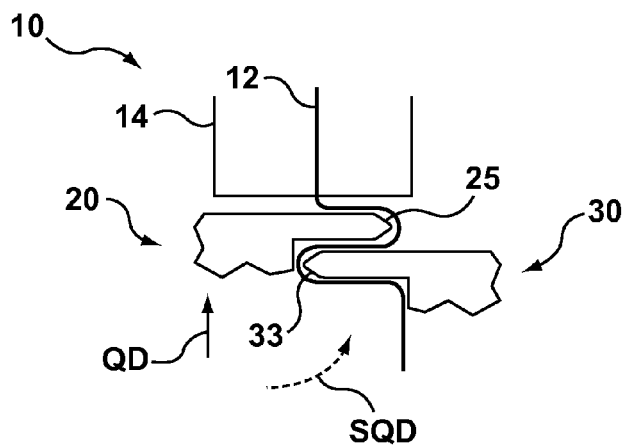
FIG. 36 is a schematic view of the forming apparatus of FIG. 35, with the first forming member and the second forming member being moved in the fourth direction.

FIG. 35 illustrates the first forming member 20 engaging the formable material 12 with the second engaging surface 25 as the first forming member 20 and the second forming member 30 are moved in the second direction SD. At the same time, or after the first forming member 20 and the second forming member 30 have been moved in the second direction SD, the first forming member 20 and the second forming member 30 are moved in the fourth direction QD, as illustrated in FIG. 36. FIG. 36 also illustrates an arc or trajectory, represented by the line SQD that the first forming member 20 and the second forming member 30 may take instead of the sequential linear movements in the second direction SD and the fourth direction QD. The second forming member 30 may be moved in the fourth direction QD to a position in between the first forming member 20 and the feeder 14, and the method depicted by FIGS. 30-36 may be repeated until the desired wave form is formed.

The first forming member 20 and the second forming member 30 may be moved away from the wave form being created at any time and rotated as illustrated in, for example, FIGS. 5A-C, 9A-C, 13A-C, 17A-C, 21A-C, and 25A-C, so that crowns of different radii may be formed. As noted above, the first forming member 20 and the second forming member 30 may also be rotated in a clockwise direction. The illustrated embodiments are not intended to be limiting in any way.

It has been found that the method of creating the wave form that is illustrated in FIGS. 30-36 forms struts that may be perfectly straight, or very close to being perfectly straight, and the struts may be formed without being drawn over one of the engaging surfaces. Drawing the formable material over one of the engaging surfaces may create struts in the wave form that may be slightly curved.

The steps illustrated in the embodiment of FIGS. 2-27 may be mixed in with the steps illustrated in the embodiment of FIGS. 28-36, as appropriate, in order to achieve the desired wave form.

Figure 37:
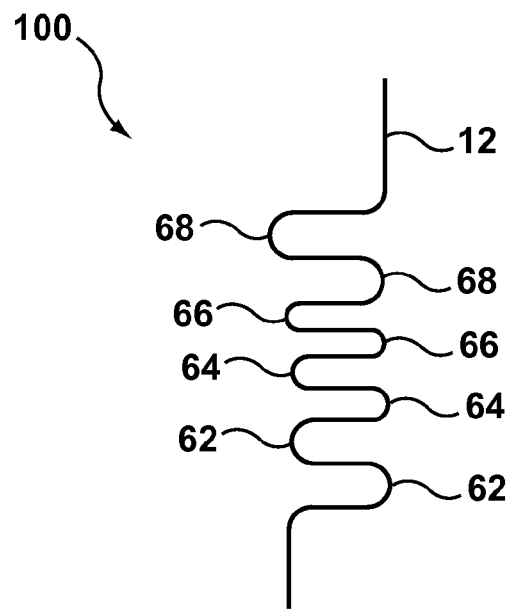
FIG. 37 illustrates an embodiment of a wave form generated by the forming apparatus of FIGS. 1-36.

After the apparatus has completed the methods illustrated by FIGS. 2-27 and FIGS. 28-36, a wave form 100 having a plurality of waves including crowns, or curved portions, and substantially straight segments is formed, as illustrated in FIG. 37. As illustrated, the wave form includes two crowns 62 that have a first radius, as defined by the first engaging surfaces 23, 33, two crowns 64 that have a second radius, as defined by the second engaging surfaces 25, 35, two crowns 66 that have a third radius, as defined by the third engaging surfaces 27, 37, and two crowns 68 that have a fourth radius, as defined by the fourth engaging surfaces 29, 39. By having forming members 20, 30 with engaging portions having engaging surfaces defined by different radii, the radii of the crowns within the wave form 100 may be varied.

Figure 38:
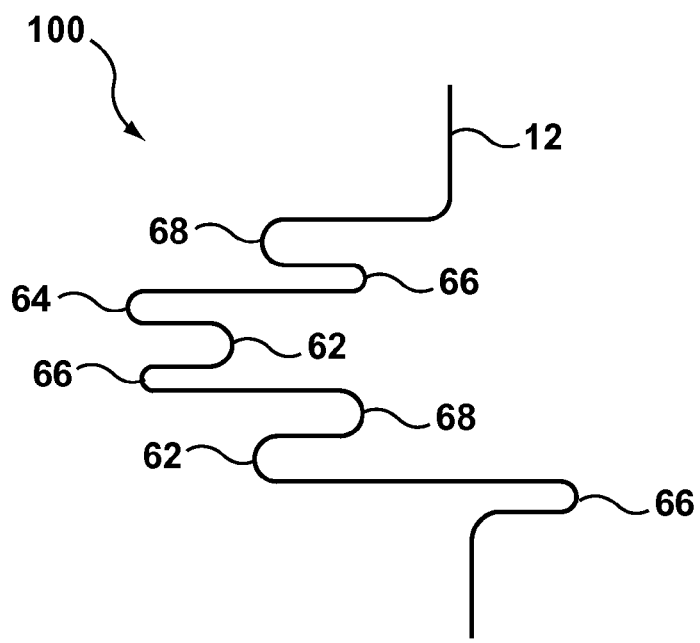
FIG. 38 illustrates an embodiment of a wave form generated by the forming apparatus of FIGS. 1-36.

Although the wave form 100 illustrated in FIG. 37 includes two crowns having the same radius next to each other along the wave form 100, the apparatus 10 may be controlled to provide any desired wave form 100 that includes crowns 62, 64, 66, 68 in any order. Also, although four engaging surfaces are illustrated for each forming member, more or less engaging surfaces may be provided. In addition, the lengths of the substantially straight segments may be varied by controlling the movement of the first and second forming members 20, 30 in directions perpendicular to the axis AX and/or by providing engaging portions 22, 24, 26, 28, 32, 34, 36, 38 having different lengths. For example, FIG. 38 illustrates a wave form 200 that may be formed by the apparatus 10. As illustrated, crowns of different radii 62, 64, 66, 68 are more random along the wave form 200, and the lengths of the substantially straight segments between the crowns are also more random, as compared to the wave form 100 illustrated in FIG. 37.

The controller 16 may be programmed with the desired wave form and corresponding signals may be communicated to the feeder 14 and the actuators 40, 50 that move the first and second forming members 20, 30, so that the first and second forming members 20, 30 are moved relative to the feeder 14 and the formable member 12 accordingly. The forming apparatus 10 uses multi-axis motions to deform the formable material 12 and create a specific wave form or stent pattern that creates a stent having substantially perpendicular ends when wound about mandrel or other suitable structure. In an embodiment, the forming apparatus uses a multi-slide to create the multi-axis motions, but it is not necessary to use a multi-slide to create such motions. Other arrangements are contemplated to be within the scope of the invention. In addition, the controller 16 may send corresponding signals to the motors or actuators that provide rotational movement to the first and second forming members to change the radii of the crowns and/or the length of the substantially straight segments.

The formable material 12 may be a wire or strip material that plastically deforms when deformed by the first and second forming members 20, 30 so that the wave form generally holds its shape after being formed. By adjusting the shape and size of the first and second forming members 20, 30, the relative motions of the first and second forming members 20, 30 in relation to each other, the formable material 12, and the feed rate or draw rate and/or movement of the feeder 14, various amplitudes, periods, and shapes may be created within the wave form to form the overall desired shape for the stent.

Embodiments of the stents made using the method and apparatus discussed above may be formed from a wire or a strip of suitable material. In certain embodiments, the stents may be formed, i.e., etched or cut, from a thin tube of suitable material, or from a thin plate of suitable material and rolled into a tube. Suitable materials for the stent include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, carbon, and magnesium, as well as combinations, alloys, and/or laminations thereof. For example, the stent may be formed from a cobalt alloy, such as L605 or MP35N®, Nitinol (nickel-titanium shape memory alloy), ABI (palladium-silver alloy), Elgiloy® (cobalt-chromium-nickel alloy), etc. It is also contemplated that the stent may be formed from two or more materials that are laminated together, such as tantalum that is laminated with MP35N®. The stents may also be formed from wires having concentric layers of different metals, alloys, or other materials. Embodiments of the stent may also be formed from hollow tubes, or tubes that have been filled with other materials. The aforementioned materials and laminations are intended to be examples and are not intended to be limiting in any way.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient roadmap for implementing an exemplary embodiment of the invention, it being understood that various changes may be made in the function and arrangement of members described in an exemplary embodiment without departing from the scope of the invention as set forth in the appended claims.

What is claimed is:

1. A method for forming a wave form for a stent, the method comprising:
   providing a length of a formable material from a supply of the formable material in a feeder along an axis in a first direction in between a first forming member and a second forming member, the second forming member being positioned closer to the feeder than the first forming member;
   moving a first forming portion of the first forming member into contact with the formable material and across the axis in a second direction substantially perpendicular to the first direction; and
   folding the formable material over a first forming portion of the second forming member by moving the second forming member and the first forming member in a third direction substantially opposite the second direction and moving the second forming member and the first forming member in a fourth direction substantially opposite the first direction;
   disengaging the first forming member from the formable material;
   rotating the first forming member, until a second forming portion of the first forming member extends in the second direction, wherein the first and second forming portions are different sizes;
   moving the second forming portion of the first forming member into engagement with the formable material at a position closer to the feeder than the second forming member;
   drawing a length of the formable member from the feeder with the first forming member and the second forming member; and
   folding the formable material over the second forming portion of the first member by moving the first forming member and the second forming member in the second direction and moving the first forming member and the second forming member in the fourth direction.

2. The method according to claim 1, wherein the first forming portion of the first forming member has a distal end having a first radius and the second forming portion of the first forming member has a distal end having a second radius that is different from the first radius.

3. The method according to claim 1, further comprising:
disengaging the second forming member from the forming material;
rotating the second forming member;
moving a second forming portion of the second forming member into engagement with the formable material at a position closer to the feeder than the first forming member;
drawing a length of the formable member from the feeder with the first forming member and the second forming member; and
folding the formable material over the second forming portion of the second forming member by moving the second forming member and the first forming member in the third direction and moving the second forming member and the first forming member in the fourth direction.

4. The method according to claim 1, wherein the second forming member and the first forming member are moved in the third direction and then are moved in the fourth direction sequentially.

5. The method according to claim 1, wherein the second forming member and the first forming member are moved in the third direction and in the fourth direction simultaneously.

6. The method according to claim 1, wherein engaging surfaces of the first and second forming portions are different sizes.

7. The method according to claim 6, wherein the engaging surfaces of the first and second forming portions are defined by different radii.

8. A method for forming a wave form for a stent, the method comprising:
providing a length of a formable material from a supply of the formable material in a feeder along an axis in a first direction in between a first forming member and a second forming member, the first forming member configured to be movable along two orthogonal axes, the second forming member being positioned closer to the feeder than the first forming member;
moving a first forming portion of the first forming member into contact with the formable material and across the axis in a second direction substantially perpendicular to the first direction; and
folding the formable material over a first forming portion of the second forming member by moving the second forming member and the first forming member in a third direction substantially opposite the second direction and moving the second forming member and the first forming member in a fourth direction substantially opposite the first direction;
disengaging the first forming member from the formable material;
rotating the first forming member in a plane defined by the two orthogonal axes;
moving a second forming portion of the first forming member into engagement with the formable material at a position closer to the feeder than the second forming member;
drawing a length of the formable member from the feeder with the first forming member and the second forming member; and
folding the formable material over the second forming portion of the first member by moving the first forming member and the second forming member in the second direction and moving the first forming member and the second forming member in the fourth direction.

9. The method according to claim 8, wherein the first forming portion of the first forming member has a distal end having a first radius and the second forming portion of the first forming member has a distal end having a second radius that is different from the first radius.

10. The method according to claim 8, further comprising:
disengaging the second forming member from the forming material;
rotating the second forming member;
moving a second forming portion of the second forming member into engagement with the formable material at a position closer to the feeder than the first forming member;
drawing a length of the formable member from the feeder with the first forming member and the second forming member; and
folding the formable material over the second forming portion of the second forming member by moving the second forming member and the first forming member in the third direction and moving the second forming member and the first forming member in the fourth direction.

11. The method according to claim 8, wherein the second forming member and the first forming member are moved in the third direction and then are moved in the fourth direction sequentially.

12. The method according to claim 8, wherein the second forming member and the first forming member are moved in the third direction and in the fourth direction simultaneously.

* * * * *